US006824663B1

(12) United States Patent
Boone

(10) Patent No.: US 6,824,663 B1
(45) Date of Patent: Nov. 30, 2004

(54) EFFICIENT COMPOUND DISTRIBUTION IN MICROFLUIDIC DEVICES

(75) Inventor: Travis Boone, San Mateo, CA (US)

(73) Assignee: Aclara Biosciences, Inc., Mountain View, CA (US)

( * ) Notice: Subject to any disclaimer, the term of this patent is extended or adjusted under 35 U.S.C. 154(b) by 773 days.

(21) Appl. No.: 09/648,181

(22) Filed: Aug. 25, 2000

Related U.S. Application Data

(60) Provisional application No. 60/151,022, filed on Aug. 27, 1999.

(51) Int. Cl.[7] ...................... G01N 27/26; G01N 27/447; B01L 11/00; C12M 1/34; C12M 1/42

(52) U.S. Cl. ....................... 204/601; 204/450; 204/451; 204/600; 422/99; 422/100; 435/288.4; 435/288.5; 435/288.6

(58) Field of Search ................................ 204/450, 451, 204/452, 453, 454, 455, 600, 601, 602, 603, 604, 605; 435/288.4, 288.5, 288.6; 422/99, 100

(56) References Cited

U.S. PATENT DOCUMENTS 6,143,152 A * 11/2000 Simpson et al. ............ 204/451
6,623,613 B1 * 9/2003 Mathies et al. ............. 204/453
6,623,860 B2 * 9/2003 Hu et al. ................ 204/600 X
2001/0045358 A1 * 11/2001 Kopf-Sill et al. ........... 204/452
2003/0006141 A1 * 1/2003 Gerlach et al. ............. 204/601

FOREIGN PATENT DOCUMENTS

GB 2319771 A 6/1998
WO WO 00/51720 9/2000

* cited by examiner

*Primary Examiner*—Nam Nguyen
*Assistant Examiner*—John S. Starsiak, Jr.
(74) *Attorney, Agent, or Firm*—David Albagli; Stephen C. Macevicz

(57) ABSTRACT

Microfluidic devices are provided having units of 8-fold symmetry comprising 8 assay units, where a reservoir provides a common component to 8 assay units. The units can be compactly formed in a substrate to provide the ability to perform a large number of assays within a small area. The microfluidic devices find use in operations, such as assays, DNA sequence detection, etc. Various formats can be used to have the microfluidic device interrelate with microtiter well plates. Methods are provided for monitoring the flow rates/velocities of assay components and streams for comparison of results in different assay units and/or to modify the conditions to change the flow rates in particular channels.

14 Claims, 4 Drawing Sheets

Replacement Sheet

EFFICIENT COMPOUND DISTRIBUTION IN MICROFLUIDIC DEVICES

CROSS-REFERENCE TO RELATED APPLICATIONS

This application claims benefit of U.S. provisional patent application 60/151,022, filed Aug. 27, 1999 which disclosure is hereby incorporated by reference.

INTRODUCTION

1. Technical Field

The field of this invention is the design and fabrication of microfluidic devices.

2. Background

Microfluidic devices promise to be the method of use, where one wishes to use very small volumes for the interaction of compounds. The interaction may be to determine the binding affinity of one compound for another, the agonist or antagonist activity of one compound for an enzyme, surface membrane receptor, intracellular protein, etc., or to carry out one or more reactions. In many instances, one or more of the components will be scarce and/or expensive, so that one would wish to use the particular component efficiently. This means that one would wish to have the component in a small volume, where a substantial portion of such volume is used in the operation.

In many cases, there will be a common component in carrying out the operation. Particularly, in assaying for biological activity of candidate compounds, one may have a common protein, such as a receptor, transcription factor, enzyme, hormone, etc., a common cell, or a common competitor, where one wishes to utilize such entity efficiently and in a reproducible manner in a microfluidic device. Since in screening one would wish to screen a multitude of different compounds for different activities, desirably one would use a chip of small dimensions, where the space occupied by each of the individual units of the device is minimized or is organized to complement another device, such as a microtiter well plate. There is a substantial interest in providing microfluidic devices, which provide effective use of scarce common components and space, while permitting ready access of electrodes to wells.

BRIEF DESCRIPTION OF RELEVANT ART

Simpson, et a., Proc. Natl. Acad. Sci. 1998, 95, 22256-2261, and references cited therein, describe capillary array electrophoresis (CAE) devices. U.S. Pat. No. 5,800,690 describes methods for detecting the movement of entities in microfluidic device channels.

SUMMARY OF THE INVENTION

Microfluidic capillary array electrokinetic (CAEK) devices are provided employing individual units having four fold symmetry, each unit providing four separate subunits permitting two independent determinations, where four subunits share a single supply reservoir for a total of 8 determinations. Units share waste reservoirs, where the waste reservoirs are distributed for positioning of electrodes for electrokinetic movement of the components of an operation. Detectors may be positioned, either fixed or movable, to address each of the main or assay channels for a determination of the result of the operation. Chips are provided which allow for a 96- or 384-assay or higher assay format. The chips may be fabricated in accordance with conventional techniques and find particular application in screening candidate compounds for one or a few characteristics. Methods are provided for monitoring channel flow to provide accurate interactions and detection in the microchannels.

DESCRIPTION OF THE SPECIFIC EMBODIMENTS

Figure 1B:
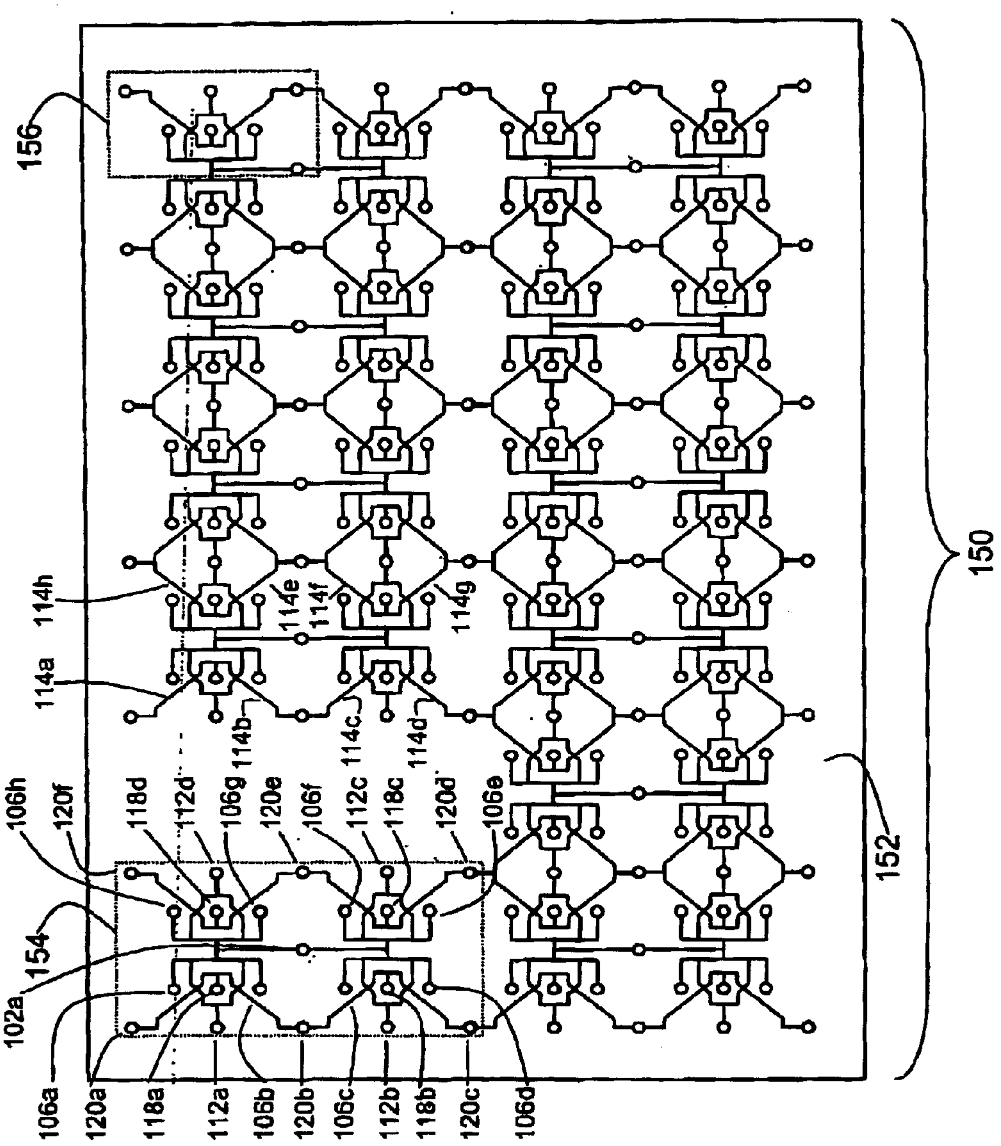
FIGS. 1*a* and 1*b* are diagrammatic plan views of a single assay unit and a microfluidic device with unit designs.

Microfluidic capillary array electrokinetic devices are provided, using efficient distribution of reagents, by employing common reservoirs. The devices have individual units comprising four individual symmetrical designs, which have all of the components for carrying out an operation, with some of the components being shared by two or more of the individual units, referred to as assay units.

Each unit is characterized by having four-fold symmetry, where each unit may be divided further into quarter-units or subunits having two single assay units to provide a total of 8-fold symmetry in relation to a common supply reservoir. Each unit has a central supply reservoir common to all of the assay units and at least one more waste reservoir shared with other units. The assay units are characterized by having a reagent source, which meets at an intersedetion, usually a T, with a compound source, frequently a test or candidate compound or a labeled reagent, and connects to a delivery channel, where unused compound and reagent are directed to a common waste reservoir. The reagent source provides reagent to 8 single assay units, i.e. four quarter-units, where the reagent is distributed to the 2 single assay units in each quarter-unit.

Each delivery channel crosses an assay channel downstream from the intersection, where the assay channel is connected at one end to a buffer reservoir and at the other end to a waste reservoir, where the waste reservoir is shared between units. By referring to a channel crossing another channel, the cross may be directly across to form an "X" or channels on opposite sides of the channel to which they are connected may be displaced, so as to form a double-T. The displacement will generally be not more than about 1 mm, usually not more than about 0.5 mm and may be 0.1 mm or less, being 0 at a direct cross and usually at least about 5 $\mu$m at a double-T.

The crosses between the assay channel and the delivery channel are on opposite sides of a buffer reservoir. The design allows for a different composition for each of the assay units, while permitting common use of reagent, buffer and waste reservoirs. The design provides that the different components used in the assay move to a waste reservoir common to four assay units, that the assay mixture may be injected into the assay channel from the delivery channel and that a common buffer reservoir provides a continuous source of liquid for transport of the assay mixture downstream toward a second common waste reservoir past a detector. The assay units will usually be associated with a single sample or test compound, with one or more assay units associated with a control.

By organizing the assay units with a single source of a component, which is common for 8 assay units, and using common reagent reservoirs and waste reservoirs, economies of use of reagents and scale may be achieved. Furthermore, as to assays performed with common reagents, e.g. buffer or assay components, there are checks that the buffer and assay components are proper and effective, since aberrant results with a group of assay units connected to the same source would indicate that the source is anomalous. Also, one may perform a control in one assay unit, which may be used as a comparison for the other assay units sharing common reagents and buffer.

Electrodes may be placed in some or all of the reservoirs to provide for electrokinetic flow of the different components of the operation. Where electrophoretic flow is employed, desirably the walls will be neutral and the components will, of necessity, be charged and of the same polarity. By contrast, if one uses electroosmotic force to move the components, then the walls of the channel will be charged, particularly the walls of the assay channel. If one wishes to use the electroosmotic force of the assay channel for moving all of the components of the operation, then by providing for appropriate cross-sections of the different channels, liquid can be made to flow from all of the reservoirs containing the operation components into the assay channel. Thus the assay channel would have a cross-section which could accommodate the volume from the other reservoirs, e.g. reagent reservoir, the compound reservoir and the buffer reservoir.

The disposition of the units is to have adjacent units aligned so as to share components of similar function. In this way, multiple units can be arranged in a device substrate that makes the most efficient use of space.

The channels for each assay unit, as well channels connecting assay units, may be all of the same cross-section or different cross-sections, depending upon the volumes to be transported through the channels, whether the cross-section of the channel will be used to control volume ratios of the different components of the operation, the rate at which the operation is run, and the like. An individual channel may have regions of different cross-section or different dimensions, e.g. width and height, for different purposes. For example, at a detection site, one may wish to have a narrow or wide dimension, depending on the manner in which the operation is evaluated. Generally, the channels may have orthogonal or angled walls, generally at an angle from about 90 to 150°, more usually about 90 to 145°. The depth will generally be in the range of about 10 to 100$\mu$, more usually about 10 to 50 $\mu$, while the width at the base will generally be in the range of about 10 to 50$\mu$ and the width at the top will generally be in the range of about 10 to 100$\mu$. Cross-section will generally be in the range of about 100 to 10,000$\mu^2$, more usually about 150 to 5,000$\mu^2$.

The dimensions of each individual unit will depend on the number of assays to be capable of being performed on a single card. The more units per unit area, the smaller dimensions, so that the dimensions will be in the lower portion of the range and concomitantly the fewer units per unit area, the greater the range of dimensions permitted for each unit. The length of the assay channel will generally be in the range of about 1 to 10 mm, more usually about 1 to 5 mm. The length of the delivery channel will generally be in the range of about 0.5 to 10 cm more usually 1 to 8 cm.

The total surface area will generally be in the range of about 9 to 200 cm2, more usually about 12 to 150 cm2. Particularly, the total surface area occupied by 12 units will usually conform to a 96 microtiter well plate, generally being 8 by 12 cm, with 9 mm spacings. By contrast where one wishes to have a 384 assay format, 96 units generally conform to a 384 microtiter well plate, being 8 by 12 cm, with 4.5 mm spacings. The dimensions of the channels and reservoirs will vary with the size of the units, where the dimensions will generally be larger, the larger the size of the unit. The volume of the reservoirs will vary depending on their function, the reagent reservoirs generally being in the range of 100 nl to 1 $\mu$l while the buffer and waste reservoirs will generally have a volume in the range of about 1 to 10 $\mu$l.

The subject devices may be fabricated from different types of materials, such as silicon, glass, quartz, polymeric substances, e.g., plastics, and the like. The device may be rigid, semi-rigid, or flexible, and may be opaque or transparent, normally having a detection region, which, as required, Will be transparent to a wavelength of interest. The devices may be prepared by any convenient microfabrication technique. Lithographic techniques can be employed in fabricating the devices, using glass, quartz or silicon substrates. These techniques are well established in the semiconductor manufacturing industries, employing photolithographic etching, plasma etching or wet chemical etching. Instead, micromachining techniques may be employed, such as laser drilling, micromilling, etc. For polymer substrates, one may use injection molding, stamp molding, or microcasting, where the substrate is polymerized within a micromachined mold. The particular choice will be based on the number of units to be produced, the sensitivity of the assay determinations to variations in the different portions of the units, and the like.

Generally, the substrate will be formed comprising open microchannels and reservoirs and having an upper planar surface where the microchannels are present as open trenches. Those portions of the microchannel and reservoir network to be enclosed, e.g. trenches, will be covered with a planar cover element. The cover element will be adhered to the substrate in a number of different ways, employing adhesives, thermal bonding, or other appropriate method. The cover element will have orifices, as appropriate, for the reservoirs and will be continuous for enclosing the channels. Where detection is performed through the cover, the cover will be transparent for the wavelength of interest at detection sites.

For the most part, detection will be achieved by detection of light, such as absorption, fluorescence or chemiluminescence, although electrical sensors can also be employed. For detecting a light signal, optical detection systems are employed, such as laser activated fluorescence detection systems, detecting the fluorescent light with a photomultiplier tube, a CCD, or the like. For absorption, spectrophotometric detection systems may be employed. Other sensors include detection of changes in conductivity, potentiometric, amperometric, etc.

The subject devices may be used in a number of different determinations. One type of determination is evaluating the characteristic of compounds in relation to a biologically active entity. The biologically active entity may be a cell, a protein, such as an enzyme, membrane receptor, transcription factor, regulatory factor, blood protein, etc., a toxin, or the like. The purpose may be high throughput screening for a library of compounds, screening compounds for toxicity, stability, side effects, interaction with other compounds, or the like. The subject devices may be used for analyzing DNA, where the assay may be the detection of a particular sequence, detection of a single nucleotide polymorphism, mutation, etc., identification of mRNA, identification of microorganisms, antibiotic resistance, etc. The assays may involve antibody binding, identifying an antibody in a sample or a ligand binding to an antibody. Other determinations may also be performed, which involve mixing two entities and determining the result of the bringing together of the two entities.

Various processes may be performed within the devices. Of particular interest are the polymerase chain reaction, ligation amplification, lysis and clean-up of the lytic products, labeling, enrichment of a mixture component, and the like.

The subject devices may be coordinated with microtiter well plates. In this embodiment, the microtiter well plates may have membrane bottoms, so that the contents of the microtiter wells may be directly moved into the reagent reservoir of the devices.

Alternatively, liquid samples may be withdrawn from the microtiter wells individually or by using a multiple transfer device.

The devices will usually have the electrodes operatively connected to a computer to control the changes in field strengths in the channels as the operation progresses. In this way, components may be moved from reservoirs into and out of channels, may be mixed at appropriate times, separated, etc. The microfluidic device may have detectors to detect the progress of particular entities along a channel and the information fed to the computer to monitor the progress of the operation and modify or correct electrical fields, as appropriate.

For further understanding of the invention, the drawings will now be considered. In FIG. 1*a* is depicted a plan view of a substrate design for an assay unit for a 96 assay format. The purpose of the assay unit is to detect the interaction between a test compound and a target compound, e.g. an enzyme. The design 100 comprises a reagent reservoir 102 connected to delivery channel 104. Joined to delivery channel 104 is test compound reservoir 106 through side channel 108, which channels join at T junction 110. The delivery channel 104 includes an incubation region or channel 105 and connects to waste reservoir 112 crossing assay channel 114 at cross-juncture 116. As indicated previously, the cross junction may be a cross where the crossing channels stay in the same line or channels on opposite sides of a straight channel may be displaced so as to form a double-T intersection, where the spacing between the two channels serves to define the volume that is injected into the straight channel, in this case the assay channel 114. Assay channel 114 connects buffer reservoir 118 to waste reservoir 120. Electrodes (not shown) are present in all of the reservoirs. Upstream from waste reservoir 120 is detector 122.

In carrying out an assay, the method will be illustrated with determining whether a compound is an agonist or antagonist to an enzyme target. The channels are filled with buffer by any convenient means, such as capillarity or pneumatic means. Enzyme in an appropriate buffer is introduced into reagent reservoir 102, the test compound and enzyme substrate into compound reservoir 106 and buffer into buffer reservoir 118. The enzyme substrate is transformed into a fluorescent product. The components of the assay are moved by electrophoretic means, so that the walls of the microchannels are neutral. For convenience, the enzyme, test compound, substrate and enzyme product have the same charge and can be moved by an electrical field in the same direction. A sieving polymer may be introduced into all of the channels. Alternatively, a monomer and a photoactivated catalyst may be introduced into the channels and selectively polymerized, particularly in the delivery channel 104 from T junction 110 to cross junction 116, as well as in assay channel 114, and the sieving polymer may be present in other portions of the channels.

Initially, electrodes in reagent reservoir 102, test compound and substrate reservoir 106 and waste reservoir 112 are activated to provide a field, which moves the enzyme, test compound and substrate into delivery channel 104 for incubation in incubation channel 105. When the components reach T junction 110, the components mix to form the assay mixture and the enzyme reacts with the substrate in relation to the effect of the test compound. The amount of enzyme product produced is related to the activity of the test compound. The field may be maintained while the enzyme is moving toward cross-junction 116 and enzyme product is continuously being produced. Further reaction may occur as the mixture is injected into the assay channel 114. When the band reaches the detector 122, the amount of product can be determined. By comparing the amount of product obtained in the absence of any test compound or in the presence of a compound of known activity, the activity of the test compound toward the enzyme can be determined.

Figure 1A:
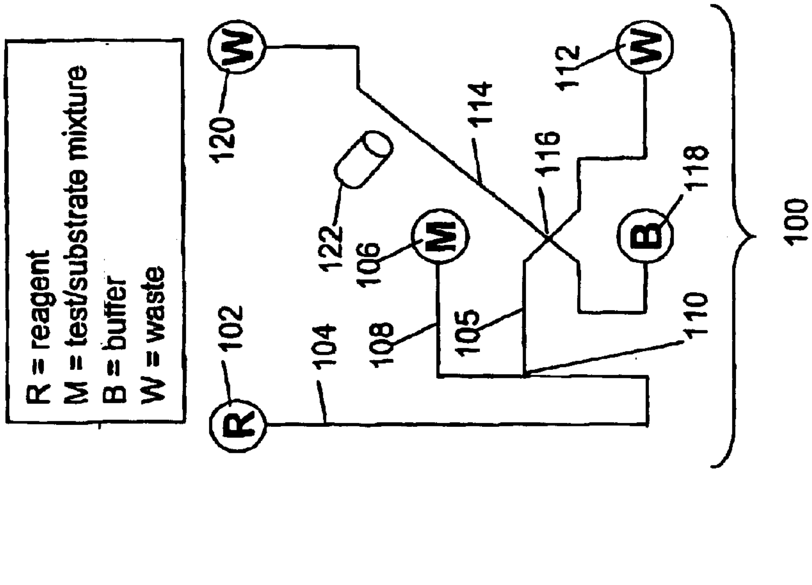

In FIG. 1*b* is shown a device 150 having substrate 152. A pattern of units 154 are shown, which is referred to as an 8-plex on a 96-assay format. The units 154 are repeated across two rows and six columns. The units 154 are eight units of 100 organized so as to share the maximum number of channels and reservoirs compatible with the purpose for which the device is used. In unit 154 there are eight test compound and substrate reservoirs 106*a–h*, associated with single assay units 100, as shown in FIG. 1*a*. The reagent reservoir 102*a* supplies the reagent to eight assay units 100, where the eight assay units are provided in four quarter-units 156. Each quarter-unit 156, individually or as part of individual unit 154, has a common buffer reservoir 118*a–d*. There are six waste reservoirs 120*a–f* associated with each unit 154 and outside the design pattern for the unit, where the waste from the assay channels 114*a–h* is directed. A single waste reservoir, e.g. 112*a*, for the delivery channel is central to the pattern of the subunit 156, receiving the waste from the two delivery channels. In this way for each subunit 156, there are a total of three waste reservoirs, two reservoirs 120 and one waste reservoir 112 available to be shared with an adjacent unit. Detection sites are closely confined and symmetrical to permit a single detection unit, such as a CCD to be employed, or be able to move detection systems along a line or row for determinations.

Figure 2A:
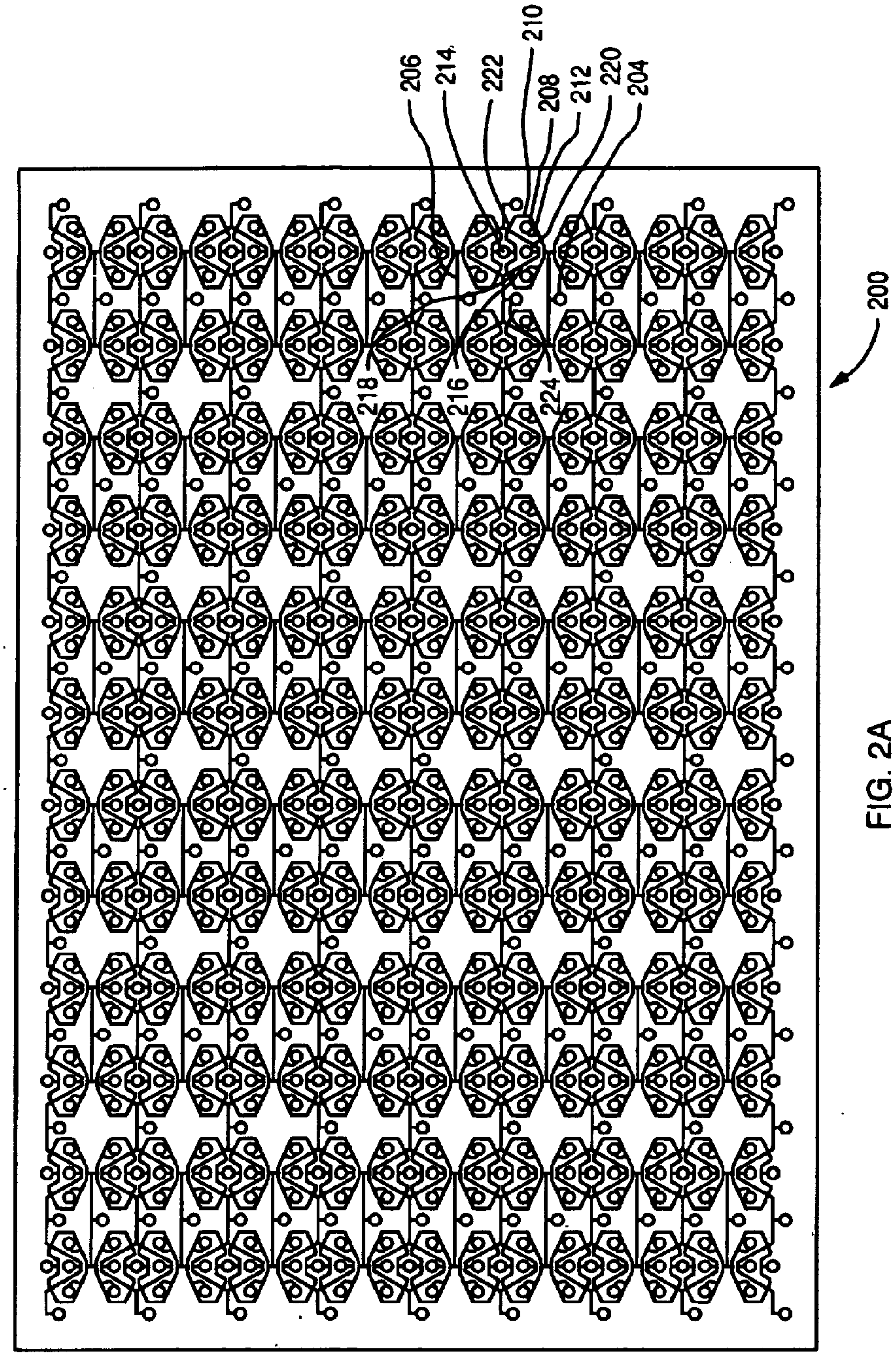
FIGS. 2*a*, 2*b* and 2*c* are respectively a diagrammatic plan view of an alternative device with a more compact design, a line drawing of an assay unit and a line drawing plan view of a unit.
Figure 2B:
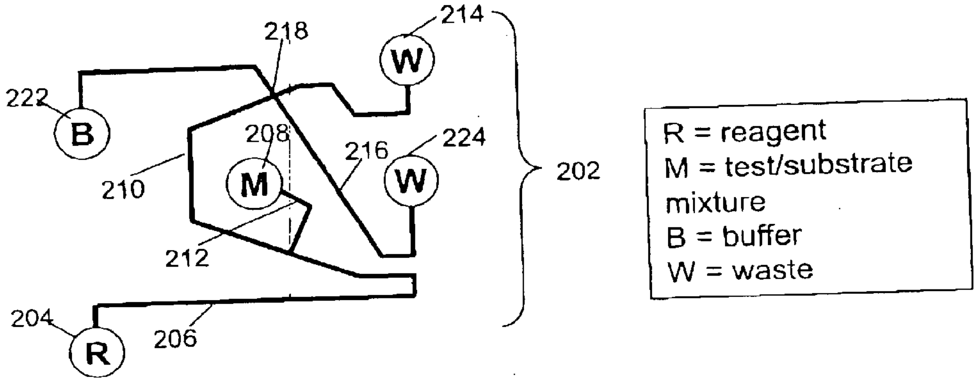
Figure 2C:
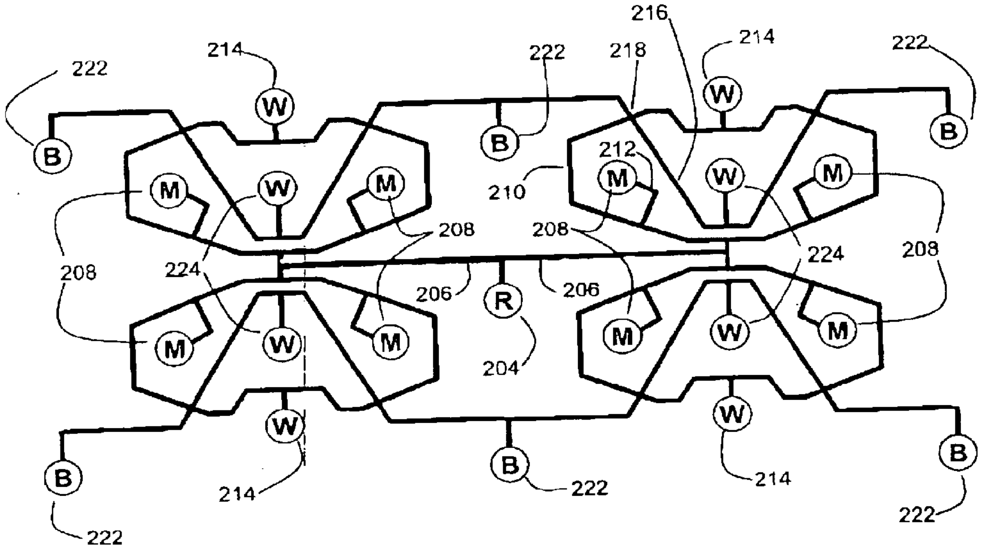

FIGS. 2*a*, 2*b* and 2*c* depict a device 200 employing a similar unit design as in FIG. 1*a*, which is organized as 8-plex symmetry for a 384-assay format. The device is broken down into a single assay unit or unit cell in FIG. 2*b* and a unit with 8-plex symmetry in FIG. 2*c*. Selecting one unit 202, the unit has a reagent reservoir 204, which supplies reagent through reagent supply channel 206. There are eight test compound reservoirs 208 symmetrically positioned. Test compound reservoir is connected to delivery channel 210 through side channel 212. Delivery channel 210 is connected to common waste reservoir 214. Delivery channel 210 connects with assay channel 216 at cross-junction 218. Assay channel 216 connects buffer reservoir 222 with waste reservoir 224.

Figure 3A:
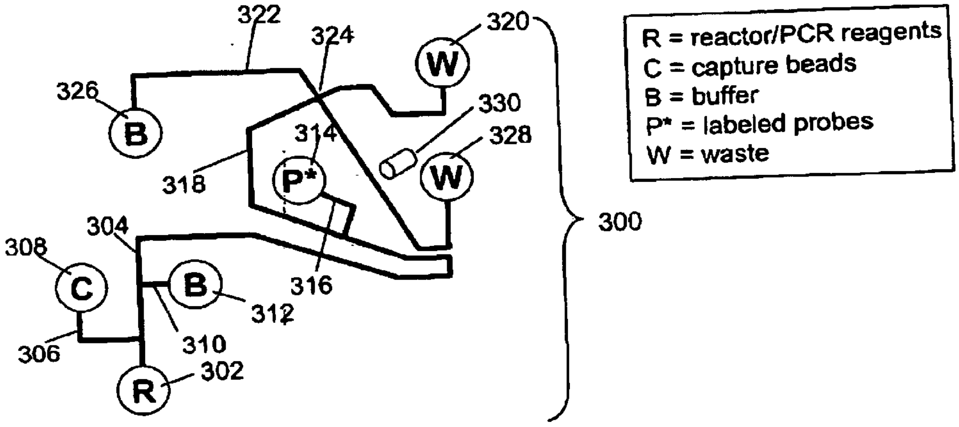
FIGS. 3*a* and 3*b* are diagrammatic plan views of a single assay unit and a single unit for performing a specific operation involving DNA analysis.

FIG. 3*a* depicts a design for using a PCR reactor and detecting specific nucleic acid sequences. The assay employs beads to capture DNA amplified in the PCR reactor, followed by contacting the captured DNA with a fluorescent probe, to determine whether a specific sequence is present.

By using primers in the PCR reactor, which have a label, which is a ligand, the amplified DNA may be captured with beads, which carry the receptor for the ligand. The beads are then contacted with the probe, which will bind to any complementary sequence bound to the beads. Excess probe is transported to the waste reservoir. The beads may then be trapped by an appropriate trap, such as a weir, or if the beads are superparamagnetic, by a magnet. The probes may then be released and detected by a detector, as indicative of the presence of the complementary sequence.

As shown in FIG. 3*a*, the network assay unit 300, has a reactor reservoir 302, which for the purposes of the present illustration is a PCR reactor. The reactor is equipped for thermal cycling (not shown). The sample DNA and reagents, namely DNA polymerase, probes and dNTPs, in an appropriate buffer, are introduced into reactor reservoir 302, and a number of thermal cycles performed resulting in the amplification of target DNA. The PCR reactor 302 is connected through delivery channel 304 and through side channel 306 to capture bead reservoir 308 and through delivery channel 304 and side channel 310 to buffer reservoir 312. Delivery channel 304 continues in a tortuous route, where labeled probe reservoir 314 is connected through side channel 316 to delivery channel 304. After the connection with side channel 316 delivery channel 304 has a bead trap region 318. The delivery channel 304 continues through bead trap region 318 to waste reservoir 320. Delivery channel 304 crosses assay channel 322 at a cross-junction 324. Assay channel 322 connects buffer reservoir 326 to waste reservoir 328. The assay channel 322 passes detector 330 upstream from waste reservoir 328. Electrodes (not shown) are present in the different reservoirs.

In carrying out the assay, charged beads are employed of a size in the range of about 5 to 100$\mu$. Electrophoresis is used for moving the beads and a sieving polymer is used in the channels. The channels are filled with an appropriate electrophoretic buffer, prior to beginning the operation. The charged beads have capture probes specific for one or more nucleic acid sequences of interest, each bead being specific for only a single sequence. The assay is carried out by introducing the sample into reactor reservoir 302 with all of the reagents necessary for amplification of one or more target sequences, if present in the sample. After thermal cycling under PCR conditions, any target DNA will be amplified. By having electrodes in reactor reservoir 302 and waste reservoir 320 of opposite polarity activated to provide a voltage of about 200 to 2000 kvolts across the delivery channel, nucleic acids present in the reactor reservoir 302 will be moved into delivery channel 304. An electrode in capture bead reservoir 308 of opposite polarity to the electrode in waste reservoir 320 is then activated to move the charged beads through side-channel 306 into delivery channel 304 to encounter the amplified nucleic acid from reactor reservoir 302. The transportation may be terminated while the beads and nucleic acid hybridize, so that nucleic acid homologous with the probes present on the beads are captured.

A voltage may then be applied to move the beads past the intersection of the delivery channel 304 and the side channel 310 from the buffer reservoir 312. The electrode in buffer reservoir may then be activated and the electrodes in reactor reservoir 302 and bead reservoir 308 allowed to float. The field created between the buffer reservoir 312 and the waste reservoir 320 controls the movement of the beads carrying the captured DNA. As the beads move through delivery channel 304, the beads encounter labeled probes from labeled probe reservoir 314, which are moved into delivery channel 304 by activating an electrode in labeled probe reservoir 314 of opposite polarity to the waste reservoir 320 electrode. The labeled probes will bind to homologous DNA bound to the beads. If target DNA has been amplified it will provide a sandwich between the beads and the labeled probe. The beads continue to move electrokinetically, either under the electrical field imposed to the bead trap region 318 (electrophoretically) or under electroosmotic force (under the electrical field or by electroosmotic pumping). The bead trap may be a physical or chemical trap. A weir or other obstruction, e.g. magnetic beads forming a porous wall, may be present in the channel at the bead trap region 318. Alternatively, the beads may be conjugated with a ligand and a receptor for the ligand may be bound at the bead trap region 318, where the receptor will capture the ligand and retain the beads at that site. The complex between the target DNA and the labeled probe is then released from the beads by any convenient means. For example, a photolytically labile bond can link the probes bound to the beads, so by irradiating the beads, the bead probe, target DNA and labeled probe complex is released. Alternatively, the melting temperature between the capture probe and the target DNA and between the labeled probe and the target DNA may be much lower, allowing for release of the target DNA bound to the labeled probe from the beads at a temperature between the two melting temperatures. As an alternative, only the labeled probe may be released by various techniques, such as having the melting temperature reversed, providing for a convenient restriction site for cleaving the dsDNA between the labeled probe and the target DNA, etc. The particular technique employed is not critical to this invention.

Once the labeled probe is released from the beads, it is then moved from the bead trap region 318 by means of the electrical field to the cross-intersection 324 between the delivery channel 304 and the assay channel 322. By changing the electrical field from across the delivery channel 304 to across the assay channel 322, the slug at the intersection 324 containing the labeled probes can be transported into the assay channel 322 toward the detection system, the buffer reservoir 326 providing the fluid for the movement in the assay channel 322. When the labeled probes move past the detector 330, the label may be detected, indicating the presence of a particular sequence in the DNA sample. Depending on the purpose of the assay and the labeled probes, the method may be multiplexed, so that a number of differently labeled probes, which can be independently detected in relation to a particular sequence, may be detected to define specific sequences in the sample DNA.

Figure 3B:
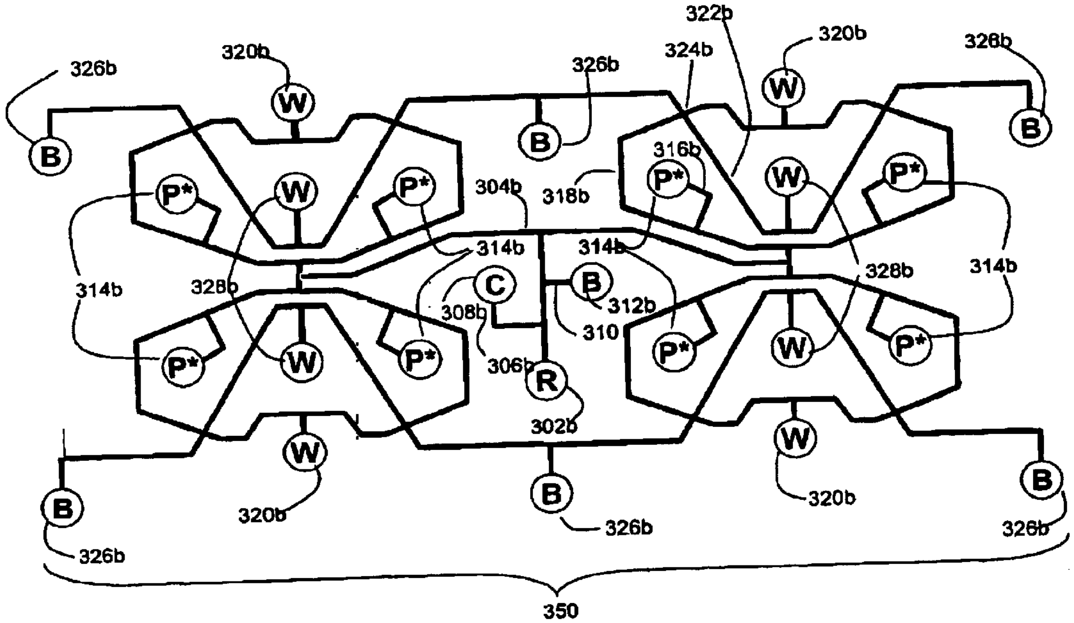

In FIG. 3*b*, a unit consisting of eight assay units depicted in FIG. 3*a* is shown. The unit 350*b* employs a reagent constituent comprising a reagent reactor 302*b*, particularly in the present illustration, a PCR reactor, a capture bead reservoir 308*b*, a buffer reservoir 312*b*, connected together through delivery channel 304*b* and side channels 306*b* and 310*b*. The delivery channel 304*b* feeds the amplified DNA from the PCR reactor 302*b* partially bound to the beads from bead reservoir 308*b* to eight different assay units 300, as shown in FIG. 3*a*. *Considering only one of the assay units in view of the symmetry of the system, labeled probe reservoir 314b* feeds labeled probe through side channel 316*b* into delivery channel 304*b* to bind to DNA captured by the beads from bead reservoir 308*b*. The beads with the sample DNA and labeled probe, if the assay is positive, are captured by the bead trap 318*b*. The labeled probe is then released from the beads and transported to the delivery channel 304*b* and assay channel 322*b* cross-intersection 324*b*. The labeled probe is injected into the assay channel 322*b* by means of buffer from buffer reservoir 326*b* and the electrical field provided by electrodes in buffer reservoir 326*b* and waste reservoir 328*b*. A detector detects the passage of the labeled probe through the assay channel 322*b*.

When using microfluidic devices, there is an interest in knowing the movement of components of an operation to ensure proper mixing, when to read a particular result, incubation times, and the like. Where, as here, there is a common source of a reagent, in order that the comparison between the results obtained at different assay units be accurate, it is important that the reagent arrive at the site where the reagent encounters the test compound at about the same time or that one can accommodate for the different times of arrival and that the reaction mixture injected into the assay channel can be monitored to coordinate readings. There is also interest in monitoring the time of mixing of operation components, the time of travel to the detector, and the like. Different methods and agents may be used, depending on the context in which the information is desired. Therefore, a detectable agent may be introduced into a reservoir, typically, a reagent source or a test compound source, or a channel downstream from the reagent source and the elapsed time determined for the detectable agent to travel from the site of introduction to the detection site. Where there are discrepancies in channel flow rates, the flow rates may be modified by changing the voltage gradients in one or more channels to equalize the system.

In one embodiment, a fluorophore is pulsed into the stream in a channel. The time for the pulse to reach a detection point gives the reagent velocity/flow rate. The superposition of electroosmotic force/electrophoresis velocity (EO/EP) is provided, unless the fluorophore is neutral. A modification is to have a fluorophore present in each reagent stream. The reagent plug chased by buffer is sampled through each pathway prior to mixing/incubation/injection. The time for the plugs to reach the detection point gives the reagent velocity/flow rate. The relative mobility of a common reagent, e.g. enzyme is known. The superposition of the EO/EP velocity is provided, unless the fluorophore is neutral. By having separately detectable fluorophores with each reagent, the fluorophore ratios will indicate the ratios of the reagents. Alternatively, one may use caged fluorophores with each reagent, which may be excited in each reagent stream. The time for the uncaged bands to reach the detection point can then be used for the velocity/flow rate analysis. Rather than using fluorophores, one may use beads, which can be detected, by light scatter, light absorption, or other detection method. Where a physical component is not desirable, one may use a thermal pulse, which can be detected over a short duration. By knowing the time when the heat was introduced into the stream and the time it took for the thermal pulse to reach a temperature sensor, e.g. a thermistor, the flow rate for the stream may be determined. Finally, one may determine the resistivity of a channel or portion of a channel as indicative of the channel uniformity or presence of constrictions. The resistivity will be relatively insensitive to small defects and small constrictions. This technique will not give information concerning local surface charge variations, so that it will not accurately predict electroosmotic force.

It is evident that the subject invention allows for the efficient use of space in a microfluidic device, permits determinations to be multiplexed on a single card, and provides efficient utilization and distribution of components used in the operations. Thus, comparison of results is improved, since one of the essential components of the operation is common to eight different determinations, providing an assurance that the component is functional, particularly when there is a control among the eight assay units.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A microfluidic device formed from a substrate, said device comprising a plurality of individual units in said substrate, each individual unit comprising 4 subunits, where the 4 subunits have 4-fold symmetry, said units further characterized by:

a common supply reservoir containing a target compound for said 4 subunits; and each subunit comprising:

a compound reservoir containing a test compound;

a delivery channel connecting with both the common supply reservoir and the compound reservoir such that the test compound and the target compound form an assay mixture when such test compound and target compound are transported through the delivery channel;

an assay channel connecting a buffer reservoir and a waste reservoir and crossing the delivery channel to form a cross-intersection for injecting the assay mixture from the delivery channel into the assay channel, the assay mixture being transported along the assay channel toward the waste reservoir for detection.

2. A microfluidic device according to claim 1, wherein said common supply reservoir comprises a PCR reactor, a bead reservoir and buffer reservoir.

3. A microfluidic device according to claim 1, wherein said substrate is plastic.

4. A microfluidic device according to claim 1, having at least about 96 assay channels.

5. A microfluidic device according to claim 1, wherein said cross-intersection is a double-T intersection.

6. A microfluidic device according to claim 1, comprising 12 of said units.

7. A microfluidic device formed from a substrate, said device comprising a plurality of individual units in said substrate, each unit comprising 8 single assay units, where the 8 assay units have 8-fold symmetry, said units further characterized by:

a common supply reservoir containing a target compound for said 8 assay units;

each assay unit comprising:

a compound reservoir containing a test compound;

a delivery channel in fluid communication with both said common supply reservoir and said compound reservoir, such that a test compound and a target compound form an assay mixture when such test compound and target compound are transported through the delivery channel;

an assay channel fluidly connecting a buffer reservoir and a waste reservoir and crossing the delivery channel to form a cross-intersection for injecting the assay mixture from the delivery channel into the assay channel, the assay mixture being transported along the assay channel toward the waste reservoir for detection; and electrodes associated with a plurality of reservoirs operatively connected to a computer.

8. A microfluidic device according to claim 7, wherein said delivery channel and said assay channel differ in at least a portion of said channels in cross-section.

9. A microfluidic device according to claim 7, comprising 96 assay channels.

10. A microfluidic device according to claim 7, wherein said cross-intersection is a double-T intersection.

11. A microfluidic device according to claim 7, comprising 384 assay channels.

12. A method for performing multiple assays, each assay involving a target compound and a test compound, in a microfluidic device comprising a plurality of individual units having (a) a common supply reservoir containing the target compound, (b) four separate subunits having 4-fold symmetry, each subunit comprising a compound reservoir containing the test compound, a delivery channel connecting with the supply reservoir and the compound reservoir, and an assay channel connecting a buffer reservoir and a waste reservoir and crossing the delivery channel to form a cross-intersection, said method comprising:

combining the target compound with the test compound in the delivery channel to form an assay mixture that produces a product;

injecting the assay mixture from the delivery channel into the assay channel at the cross-intersection;

transporting the assay mixture through the assay channel; and detecting the product, thereby performing multiple assays.

13. A method according to claim 12, wherein a control assay is performed in at least one said assay channel within said unit.

14. A method according to claim 12, wherein said target compound is an enzyme.

* * * * *